United States Patent
Wodajo

(10) Patent No.: US 11,006,969 B2
(45) Date of Patent: May 18, 2021

(54) PATIENT-SPECIFIC CUTTING GUIDE

(71) Applicant: Felasfa Wodajo, Potomac, MD (US)

(72) Inventor: Felasfa Wodajo, Potomac, MD (US)

( * ) Notice: Subject to any disclaimer, the term of this patent is extended or adjusted under 35 U.S.C. 154(b) by 212 days.

(21) Appl. No.: 15/896,284

(22) Filed: Feb. 14, 2018

(65) Prior Publication Data
US 2018/0368860 A1 Dec. 27, 2018

Related U.S. Application Data

(60) Provisional application No. 62/541,701, filed on Aug. 5, 2017, provisional application No. 62/514,952, filed on Jun. 4, 2017.

(51) Int. Cl.
*A61B 17/17* (2006.01)
*A61B 17/15* (2006.01)
(Continued)

(52) U.S. Cl.
CPC .......... *A61B 17/1703* (2013.01); *A61B 17/15* (2013.01); *A61B 34/20* (2016.02); *A61B 90/39* (2016.02); *A61B 17/151* (2013.01); *A61B 17/152* (2013.01); *A61B 17/155* (2013.01); *A61B 17/157* (2013.01); *A61B 17/1707* (2013.01); *A61B 17/1728* (2013.01); *A61B 17/1739* (2013.01); *A61B 17/1764* (2013.01); *A61B 2017/568* (2013.01); *A61B 2034/108* (2016.02); *A61B 2090/363* (2016.02);
(Continued)

(58) Field of Classification Search
CPC ............ A61B 17/1703; A61B 17/1707; A61B 2017/568; A61B 90/39; A61B 2090/363; A61B 2090/376; A61B 2090/3966; A61B 2090/3983; A61B 2034/108; A61B 17/15; A61B 17/151; A61B 17/152; A61B 17/154; A61B 17/155; A61B 17/157; A61B 17/158; A61B 17/1675; A61B 17/17; A61B 17/1702; A61B 17/1728; A61B 17/1739; A61B 17/1764
USPC .......................................................... 606/96
See application file for complete search history.

(56) References Cited

U.S. PATENT DOCUMENTS 6,711,432 B1 * 3/2004 Krause .................. A61B 17/15
128/922
7,744,600 B2  6/2010 Rangaiah et al.
(Continued)

FOREIGN PATENT DOCUMENTS

WO  2017091380 A1  6/2017

*Primary Examiner* — Marcela I. Shirsat
(74) *Attorney, Agent, or Firm* — Charney IP Law LLC

(57) ABSTRACT

A patient-specific cutting guide system comprises at least two instruments. One is a positioner configured to locate a fiducial marker on a patient's bone and to be secured in three axes. The second is a cutting guide that cooperates with the positioner and delineates cuts to be made. The instruments are designed from images of the bone with the marker already in place. Preferably, a positioner comprises at least three targeting apertures configured to locate at least three non-linear markers. The cutting guide comprises top surface contours that guide the depth of the cuts. A method of forming this system comprises placing at least one marker (preferably three) on a patient's bone, then imaging the bone, forming a positioner designed to incorporate the marker position, and forming a cutting guide configured to be oriented and anchored by the positioner.

37 Claims, 5 Drawing Sheets

(51) Int. Cl.
*A61B 34/20* (2016.01)
*A61B 90/00* (2016.01)
*A61B 34/10* (2016.01)
*A61B 17/56* (2006.01)

(52) U.S. Cl.
CPC . *A61B 2090/376* (2016.02); *A61B 2090/3966* (2016.02); *A61B 2090/3983* (2016.02)

(56) References Cited

U.S. PATENT DOCUMENTS

| | | |
|---|---|---|
| 7,794,467 B2 | 9/2010 | McGinley et al. |
| 9,317,631 B2 * | 4/2016 | Davison ............... A61B 17/151 |
| 9,668,747 B2 | 6/2017 | Metzger et al. |
| 9,700,329 B2 | 7/2017 | Metzger et al. |
| 2005/0234465 A1 | 10/2005 | McCombs et al. |
| 2009/0088758 A1 * | 4/2009 | Bennett ................ A61B 17/157 606/82 |
| 2010/0168799 A1 * | 7/2010 | Schumer ............ A61B 17/8014 606/286 |

* cited by examiner

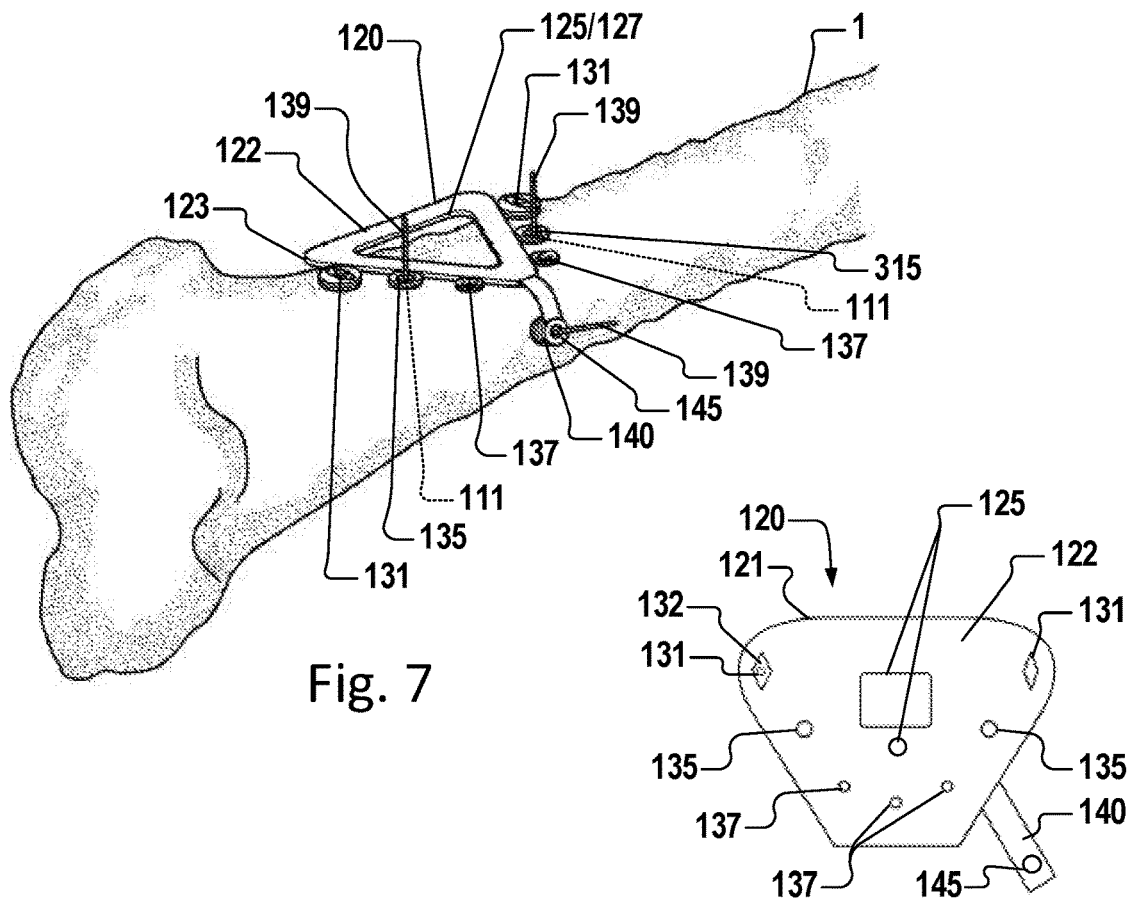
Fig. 7
Fig. 8
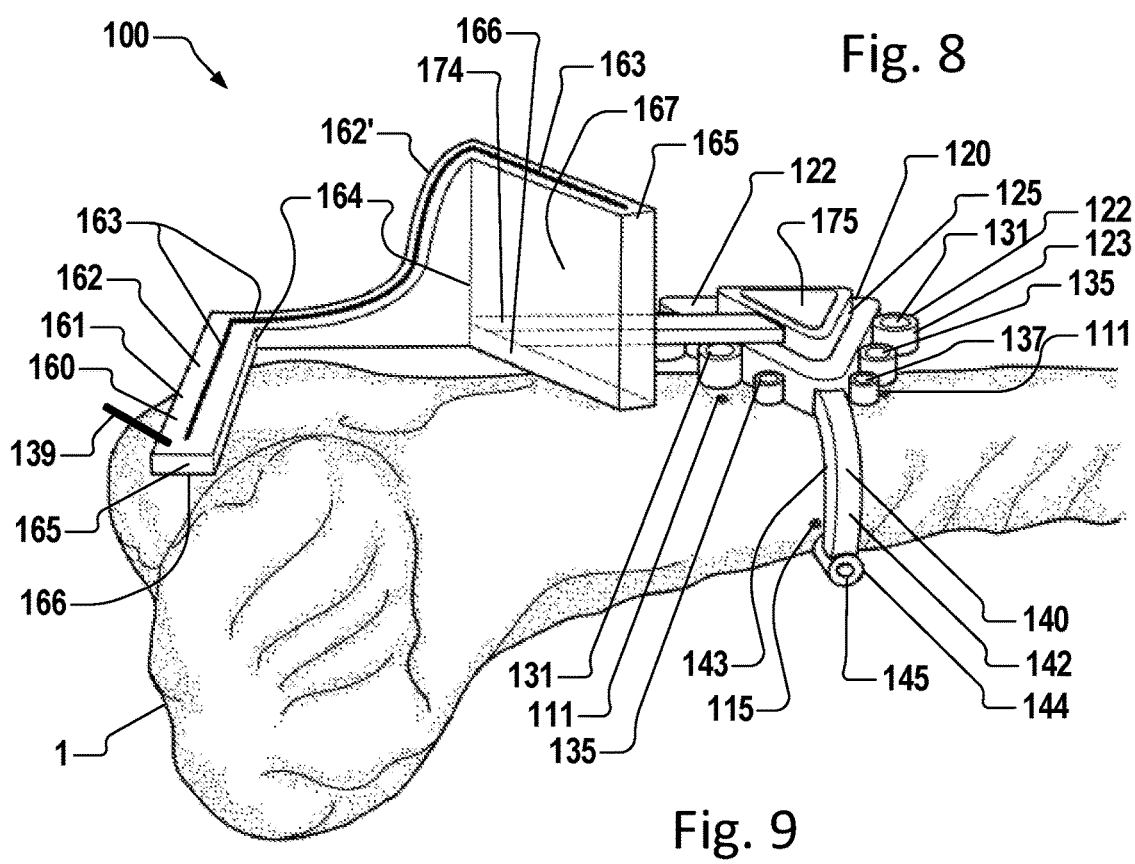
Fig. 9

PATIENT-SPECIFIC CUTTING GUIDE

RELATED APPLICATIONS

This application claims the benefit of and herein incorporates by reference U.S. Provisional Patent Application No. 62/541,701, filed on Aug. 5, 2017, entitled "Patient Specific Instrument Augmented with Radiologic Imaging, for Use in Precisely Cutting Bones in a Variety of Settings," and also claims the benefit of U.S. Provisional Patent Application No. 62/514,952, filed on Jun. 4, 2017, entitled "Navigated Patient Specific Instrument, for Use in Precisely Cutting Bones in a Variety of Settings," which is also incorporated by reference.

FIELD

The present disclosure relates to patient-specific cutting instruments, and more particularly to systems, devices, and methods of forming custom manufactured instruments that aid in the cutting of bone to precise dimensions.

BACKGROUND

This section provides background information related to the present disclosure which is not necessarily prior art.

It is often necessary in orthopedic surgery to divide a bone accurately into two or more portions. When bones are divided for the removal of a tumor, the location of these cuts is of paramount importance. Current methods for ensuring the precision of the cuts are either burdensome or subject to inaccuracy due to improper location on the bone.

There is need in the art for a system, device, and method for locating cuts so that they are made in the intended location.

SUMMARY OF THE INVENTION

This section provides a general summary of the disclosure, and is not a comprehensive disclosure of its full scope or all of its features.

A system for a patient-specific bone cutting guide generally comprises two instruments. One instrument is a positioner configured to locate at least one fiducial marker (placed on a patient's bone) and to be secured in three axes to prevent movement. The second instrument is a cutting guide configured to cooperate with the positioner and to delineate the cuts to be made in the bone. The positioner and the cutting guide are designed from images taken of the patient's bone with one or more markers already in place. The marker(s) may or may not be considered part of the system, and the same is true of the imaging technology used to locate the marker(s). Such items may be provided separately or as a kit, along with any pegs or anchors.

In a preferred embodiment, a positioner generally comprises at least three targeting apertures configured to locate at least three markers implanted in non-linear order. At least three anchoring apertures are configured to cooperate with any necessary anchors. The cutting guide comprises top surface contours that guide the depth of the cuts. Also, bottom surface contours that match the contours of the top surface of the bone may be utilized.

A method of forming a patient-specific bone cutting guide system generally comprises placing at least one marker on a patient's bone, imaging the patient's bone with the at least one marker in place, forming a positioner designed to incorporate the position of the at least one marker (where the positioner is configured to locate the at least one marker and to be anchored in place), and forming a cutting guide configured to be oriented by the positioner and to delineate the cuts to be made in the bone. In a preferred embodiment, this method comprises placing at least three markers on the bone and forming the positioner with at least three targeting apertures, one of which is on a transverse member, and at least three anchoring apertures. More simply, this method may comprise only the steps of forming and configuring the positioner and the cutting guide from images taken of the patient's bone with the one or more markers already in place.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

A more complete understanding of these embodiments, and the attendant advantages and features thereof, will be more readily understood by reference to the following detailed description when considered in conjunction with the accompanying drawings. The drawings described herein may not be to scale, are for illustrative purposes only of selected embodiments and not all possible implementations, and are not intended to limit the scope of the present disclosure.

For clarity and in order to emphasize certain features, not all of the drawings depict all of the features that might be included with the depicted embodiment. The invention also encompasses embodiments that combine features illustrated in multiple different drawings; embodiments that omit, modify, or replace some of the features depicted; and embodiments that include features not illustrated in the drawings. Therefore, it should be understood that there is no restrictive one-to-one correspondence between any given embodiment of the invention and any of the drawings.

FIG. 7 illustrates alternate securing of the positioner of FIG. 6.

FIG. 8 illustrates optional features for the positioner.

FIG. 9 is a perspective view of a cutting guide attached to the positioner.

Corresponding reference numerals indicate corresponding parts throughout.

DETAILED DESCRIPTION

Figure 1:
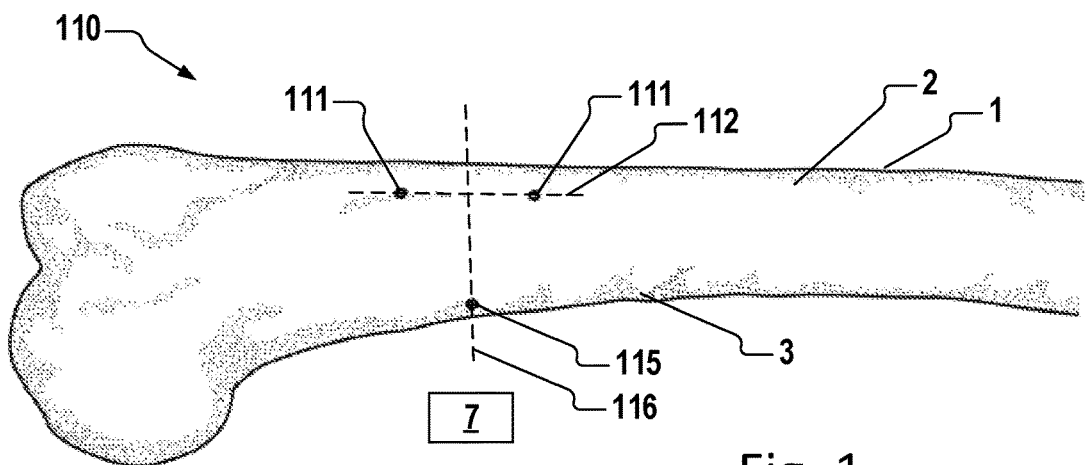
FIG. 1 is a view of a bone having three implanted fiducial markers.

Any reference to "invention" within this document is a reference to an embodiment of a family of inventions, with no single embodiment including features that are necessarily included in all embodiments, unless otherwise stated. Furthermore, although there may be references to "advantages" provided by some embodiments, other embodiments may not include those same advantages, or may include different advantages. Any advantages described herein are not to be construed as limiting to any of the claims.

As used herein, relational terms, such as "first" and "second," "top" and "bottom," and the like, may be used solely to distinguish one entity or element from another entity or element without necessarily requiring or implying any physical or logical relationship or order between such entities or elements.

Specific quantities, dimensions, spatial characteristics, compositional characteristics and performance characteristics may be used explicitly or implicitly herein, but such specific quantities are presented as examples only and are approximate values unless otherwise indicated. Discussions and depictions pertaining to these, if present, are presented as examples only and do not limit the applicability of other characteristics, unless otherwise indicated.

In describing preferred and alternate embodiments of the technology described herein, specific terminology is employed for the sake of clarity. The technology described herein, however, is not intended to be limited to the specific terminology so selected, and it is to be understood that each specific element includes all technical equivalents that operate in a similar manner to accomplish similar functions.

Example embodiments will now be described more fully with reference to the accompanying drawings. Specific details are set forth such as examples of specific components and methods to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known device structures are not described in detail.

Introduction

Every human bone is unique, and Applicant has leveraged various technologies for 3D and/or 4D scanning and printing to develop novel systems, devices, and methods for making precise cuts in bones based upon attributes that are specific to each patient. There is obvious value to both surgeon and patient when cuts in bones are made precisely and with increased ease.

In this specification, the "navigated cutting guide" or patient-specific cutting guide system 100 of FIGS. 1-12 includes a patient-specific cutting guide 160 that is itself a system and/or device that may further include a cutting guide positioner 120 that also may be a system or device. Each of these systems and devices are novel in their own right and have associated methods that are also novel. One of skill in the art will understand that related system, device, and method terminology may often be used interchangeably unless specified otherwise.

Two prior art methods are currently used to ensure the precision of cuts. The first option is burdensome and involves using an external computer-aided navigation apparatus to confirm correct location of the surgical instruments relative to the bone.

The second prior art option is to design and manufacture a patient-specific cutting guide (also known as a patient specific instrument, or "PSI") utilizing cross-sectional imaging of the bone and additive manufacturing (3D printing). The surface of the cutting guide to be placed against the bone is made to match the surface contours of the bone, and the cutting guide incorporates one or more slots to precisely guide a cutting instrument. However, there is a risk of inaccurate cuts due to improper location of the cutting guide on the bone during surgery, even with the contour match. Risk is greatest in two instances. One potential for missing the intended location of the cutting guide occurs with a tubular bone, such as the femur or tibia, where the surface is relatively devoid of surface irregularities, thus failing to ensure an identical match of the cutting guide to its location. Another potential positioning error occurs due to soft tissue covering the bone (for example, extraosseous extension of a tumor) and preventing contact between the cutting guide and the underlying bone.

Positioner for a Cutting Guide

The present invention eliminates the above described potential for inaccuracy. Beginning with FIG. 1, a bone 1 (which may include soft tissue) is prepared for surgery by placement of at least three small fiducial markers 111, 115 firmly in or on the bone 1 or adjacent tissues to serve as reference points for proper placement of a cutting guide 160, which will be described later. One of skill in the art will understand that in this specification references to "on the bone" includes the meanings of "or in the bone" and "or adjacent the surface of the bone" and "or proximate the bone." Fiducials, fiducial markers, or markers 111, 115 are small, typically radio-opaque metal (for example, stainless steel or gold) cylinders or pins that allow pinpoint guidance for medical treatment. However, markers 111, 115 are not limited to metal or specific types of metal or to specific shapes (for example, markers may be spheres, coils, or other shapes), and may include devices that emit electromagnetic or other energy for purposes of localization, provided the markers 111, 115 provide the functionality described herein.

Markers 111, 115 may be seen via any number of scanning or imaging technologies 7 generally referred to as x-ray imaging, which may include fluoroscopy, computed tomography (CT), and radiography via live moving and/or still images. An imager or imaging system/technology 7 represents these and other current or future imaging technologies that allow markers to be seen in or on a patient's body. Said imaging technology 7 is understood to be used even if not illustrated in each Figure.

To simplify the procedure, the first two markers 111 are implanted on the closest bone surface 2 to the surgeon during the planned procedure. These two markers 111 are necessarily linear and lie on at least a first plane 112 (see FIG. 6) that runs through the markers 111 to the closest portion of the floor below the patient. The third fiducial 115 cannot be co-linear (as denoted by axis and/or plane 116, which may be orthogonal to plane 112) but may be placed anywhere else on the bone, preferably on a not-too-distant bone surface 3. In other words, regardless of their positions, three or more markers 111, 115 allow triangulation 110 for placing a cutting guide positioner 120 as shown in FIG. 2.

Fiducials are implanted with a minor procedure before obtaining CT (or other) images used for designing any patient-specific instrument. The location of the markers 111, 115 on the bone 1, as visualized on the CT scan, is then incorporated into the design of the positioner 120 and cutting guide 160. These parts are then printed of medical grade materials, including plastic, carbon, composites, or a wide variety of suitable materials that are generally inflexible in order to maintain position. Scanning produces data that is then used (and may be manipulated) for printing patient-specific parts. Scanning, manipulating data, and printing may or may not be included in the methods related to these systems and devices, and manufacturing is not limited to printing.

Figure 2:
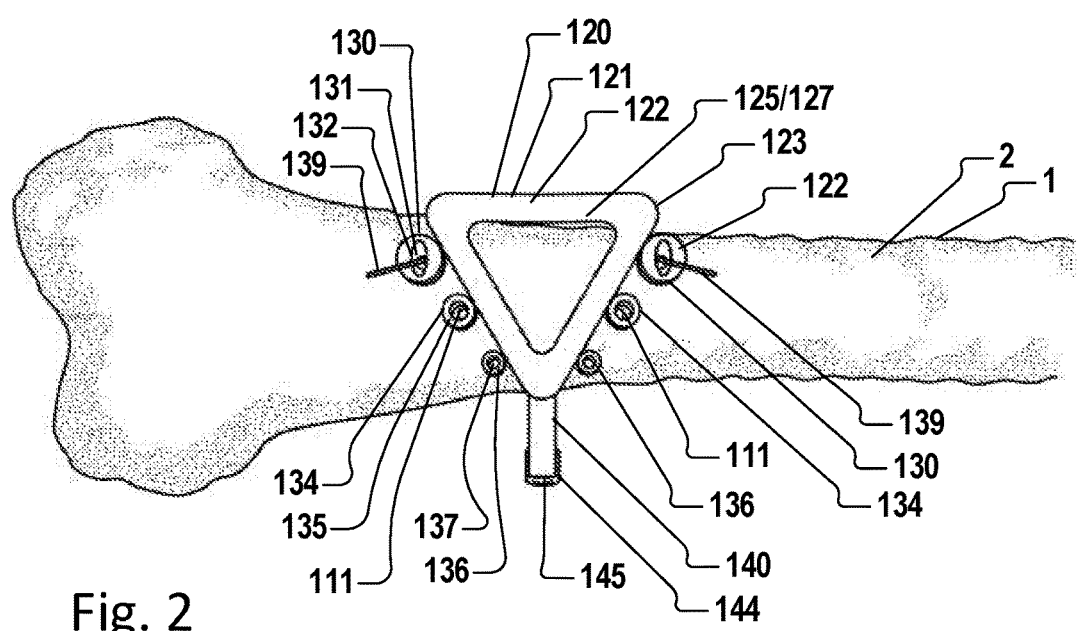
FIG. 2 is a top view of a positioner located over two markers of FIG. 1.

During a later surgery, FIG. 2 is a view of the positioner 120 placed over the bone 1. Using imaging technology 7, markers 111 are visualized. For example, with radiologic imaging such as intraoperative fluoroscopy, the "c-arm" would be positioned in the anterior-posterior (AP) plane. Once the first two fiducial markers 111 are visualized within the targeting apertures 135 of two targeting rings 134, two fixation wires or anchors 139 are driven through the anchoring apertures 131 of anchor rings 130 and into the bone 1. These two anchors 139 constrain the positioner 120 in two axes.

Figure 3:
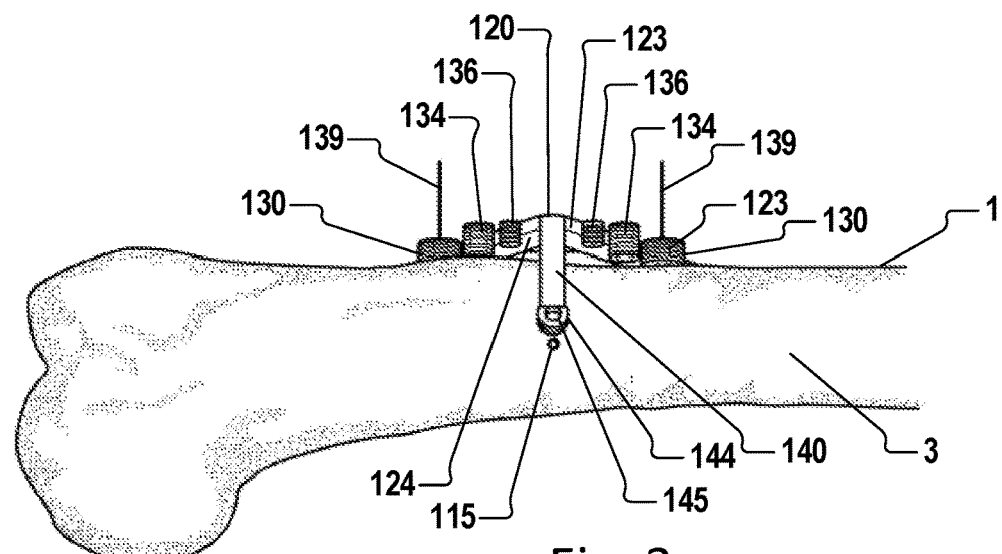
FIG. 3 an illustration of the positioner of FIG. 2 prior to location over the third marker of FIG. 1. Rd

FIG. 3 is a view at this time of the bone 1 and positioner 120 with the c-arm in the lateral position. Initially, the (transverse) third marker 115 is not correctly located within the aperture 145 of the transverse targeting ring 144.

Figure 4:
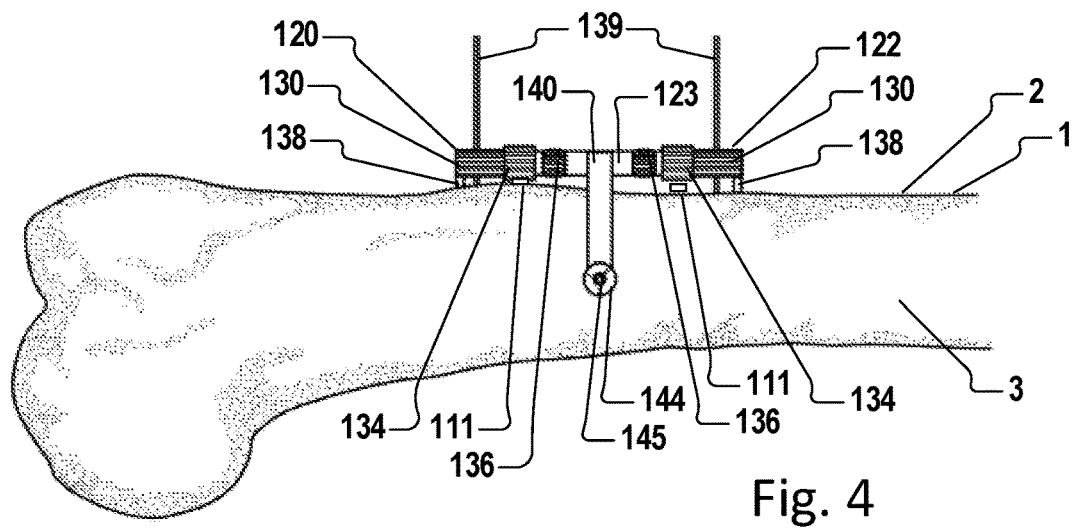
FIG. 4 is an illustration of the positioner correctly located in three axes.

In FIG. 4, the positioner 120 is rotated and transverse member 140 oriented such that the third marker 115 is accurately visualized within the transverse targeting aperture 145 of the transverse targeting ring 144.

Figure 5:
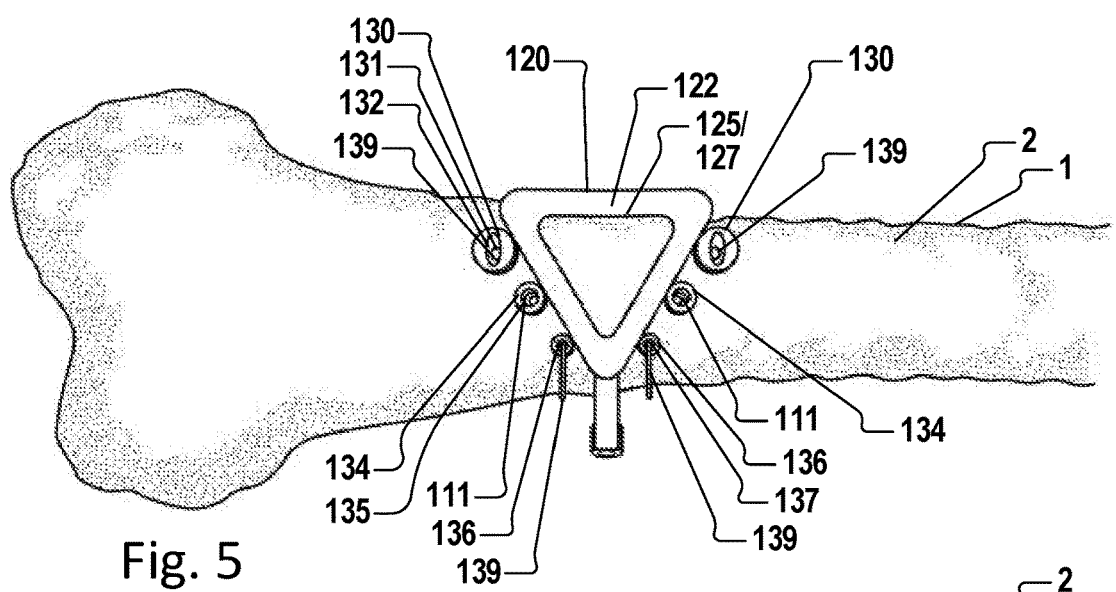
FIG. 5 is a top view of the positioner of FIG. 4 secured by anchors.

At that time, as shown in FIG. 5, and with the c-arm returned to the AP position, at least one additional anchor 139 is driven through the locking aperture 137 of the locking ring 136 and into the bone 1. Anchors 139 are preferably driven through two locking rings 136. These anchors 139 are slightly oblique to the first two anchors 139 in the anchoring apertures 130. The positioner 120 is now correctly located and firmly locked or secured in three axes.

Figure 6:
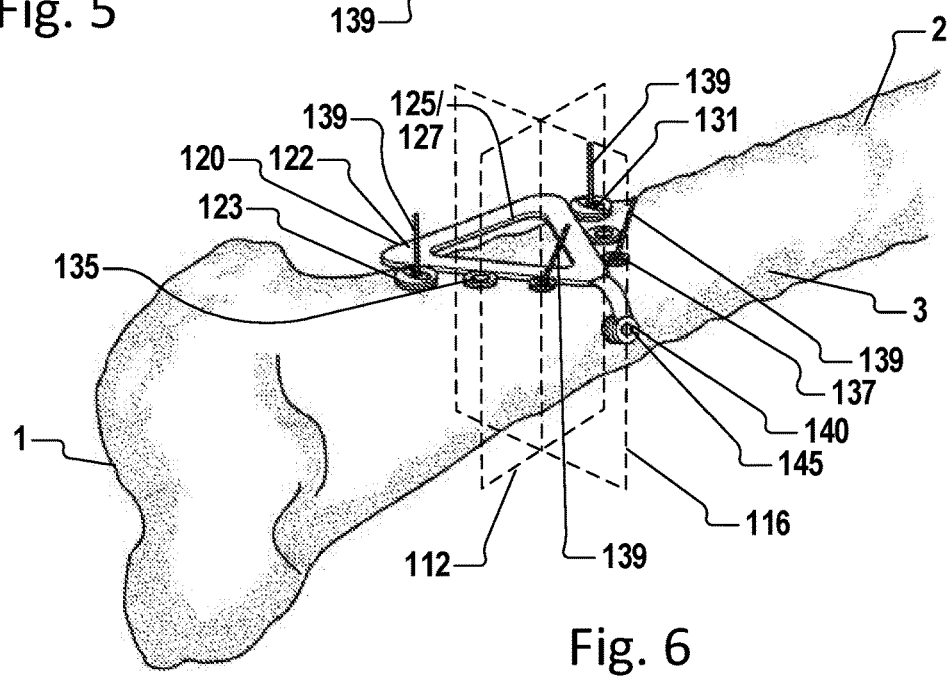
FIG. 6 is a perspective view of the positioner of FIG. 5 secured on the bone.

FIG. 6 is a perspective view of the positioner 120 secured on the bone 1 using four wires or anchors 139. FIG. 7 is the same view with alternative anchoring. In this case, the three anchors 139 are secured through the targeting apertures 135, 145 at the markers 111, 115. The markers 111, 115 may be hollow and accept the anchors 139 as they pass into the bone 1. Anchoring is not limited to wires, but may include other parts that provide similar locking functionality, such as screws. Alternatively, the markers 111, 115, anchors 139 and/or coacting parts of the positioner 120 may be magnetic, threaded, snap-like, or otherwise designed to provide comparable functionality.

FIG. 8 illustrates the basics of the positioner 120 structure and functionality. To this point, the positioner 120 has been illustrated as a triangular body 121 and rings 130, 134, and 136 with outer surface 123 (also called the side or exterior surface), plus transverse member 140 having ring 144. However, the positioner 120 is not limited to a triangular shape, nor to rings 130, 134, 136, 144. Indeed, body 121 may range from a "V" shape to an oval or rectangle, or a combination thereof, with rounded or sharp corners, and the overall shape of the positioner 120 may range from a "Y" shape to a "J" shape to other shapes having a transverse member 140. The chosen structure must maintain apertures (selected from among 131, 135, 137) for locating and anchoring the positioner 120 to bone 1. The positioner 120 may have some curvature, particularly at transverse member 140. The transverse member 140 may unibody with or attachable to the body 121. For simplicity, the drawings do not label every element of symmetrical parts, as that symmetry is understood, but the present invention is not limited to symmetrical design.

FIGS. 1-7 provide insight into several other details and alternatives. Anchoring aperture 131 may be slotted and may have an interior beveled, recessed surface 132 to allow some adjustment of the positioner's 120 orientation relative to the anchors 139. "Slotted" may be oval, diamond-shaped, or other shapes and is intended broadly to describe an aperture 131 functional to hold the positioner 120 in two axes on relative markers 111 while allowing adjustability to reach proper orientation in the third axis. The body 121, any rings, and/or the transverse member 140 may share a top surface 122/142 and/or outer surface 123/143. Pegs 138 (see FIG. 4) or similarly functional surface features will usually be placed between the bone and the bottom surface 124 of the positioner 120 to aid orientation and anchoring. Attachment aperture 125 having inner surface 127 is illustrated at the center of the positioner 120, although it is not limited to that location, and is used for connecting one or more cutting guides 160 to the positioner 120. Attachment aperture 125 may be a small hole for accepting a screw, pin, or other fastener or may be relatively large for accepting a plug 175 or similar fastener (see FIG. 9), and the inner surface 127 may hold via friction at a minimum. Although use of at least two locking apertures 137 is preferred, at times only one may be used and may be centrally located on the positioner 120 (see FIG. 8). Finally, the transverse member 140 may extend from the positioner body 121 at angles different from ninety degrees and from points other that the tip of a triangle.

Cutting Guide

Having fully described the positioner 120, we now turn to FIG. 9 to view a patient-specific cutting guide system 100. The cutting guide 160 is attached to the positioner 120, in this illustration via plug 175 pushed firmly into attachment aperture 125, wherein the plug 175 is connected to the wall 161 of the cutting guide 160 by inflexible arm 174. The plug 175, arm 174 and guide 160 may be printed or otherwise formed as one piece or may be formed separately and assembled. The cutting guide 160 may be attached to any part of the positioner 120, not being limited to its center, and at times the arm 174 may be omitted, in which case the wall 161 of the guide 160 will contact the positioner 120. This illustration omits anchors for simplicity. The cutting guide 160 itself may also be anchored to the bone 1. The positioner 120 and guide 160 may be one piece or multiple pieces.

Cutting slot(s) 163 running through the wall 161 of the guide 160 are designed to guide a cutting mechanism 190 such as a saw. Phrased another way, the wall top 161 with cutting slot 163 resembles a rail on which the cutting mechanism rides. The guide 160 may have interior walls 167, exterior walls 168, and bends 164 in the wall 161 and may have one or more stops or end walls 165 to impede a saw's progress. The cutting guide 160 is not limited to saws and linear slot shapes, as it is contemplated that other cutting mechanisms 190 (including drills) and cutting patterns may utilize a variety of guiding shapes inside or outside of the cutting guide 160.

Figure 10:
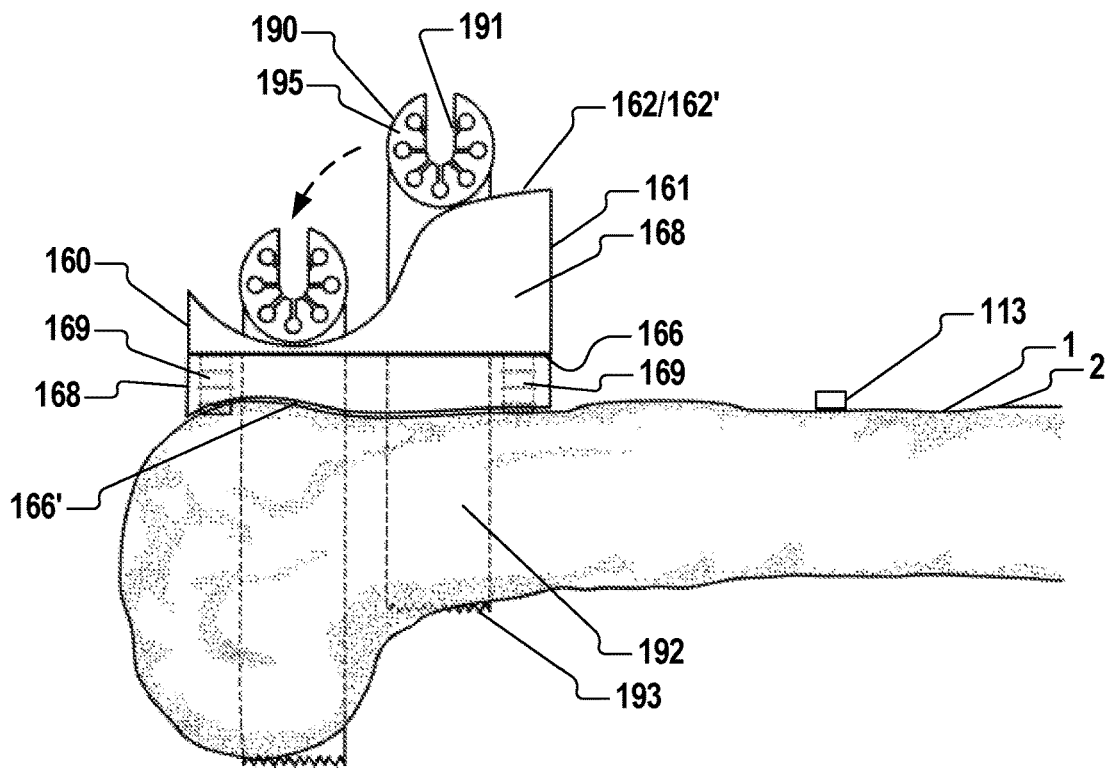
FIG. 10 illustrates a cutting guide located on a bone.

FIGS. 9-10 show a preferred embodiment of the cutting guide 160 wherein the top 162 of the wall 161 has contours 162' such that the thickness or height of the wall 161 varies in dimension in proportion to the dimensions (surface contours) of the bone 1 at that location, thus allowing for accurate cutting depth. In other words, the contours 162' are a negative of the back of the bone 1. In FIG. 10, cutting device 190 (for example, an oscillating saw having blade 192 with cutting edge 193, as well as an attachment opening 191) comprising a rounded head 195 is constrained by the wall's 161 top surface contours 162' as the top surface 162 helps the cutting device 190 navigate the guide 160. This design and method of navigation are novel. Pegs 169 may be used and modified (whether added or removed in part or in whole) between the bone 1 and the bottom surface 166 of the cutting guide 160 at the time of surgery. Alternatively, the cutting guide 160 may be formed with a bottom surface contour 166' that matches the top surface 2 contour of the bone 1 on which the guide 160 rests.

In an alternative and novel method, a cutting guide 160 having bottom surface contour 166' is designed and placed with the aid of at least one marker 113 (FIG. 9). The marker 113 acts in similar fashion to transverse marker 115 because bottom surface contours 166' themselves are not sufficient to confirm accurate guide 160 placement. Thus, a positioner 120 would need to target and anchor with reference to the at least one marker 113. The positioner 120 and arm 174 are not shown in FIG. 10, but their use has been discussed.

Figure 11:
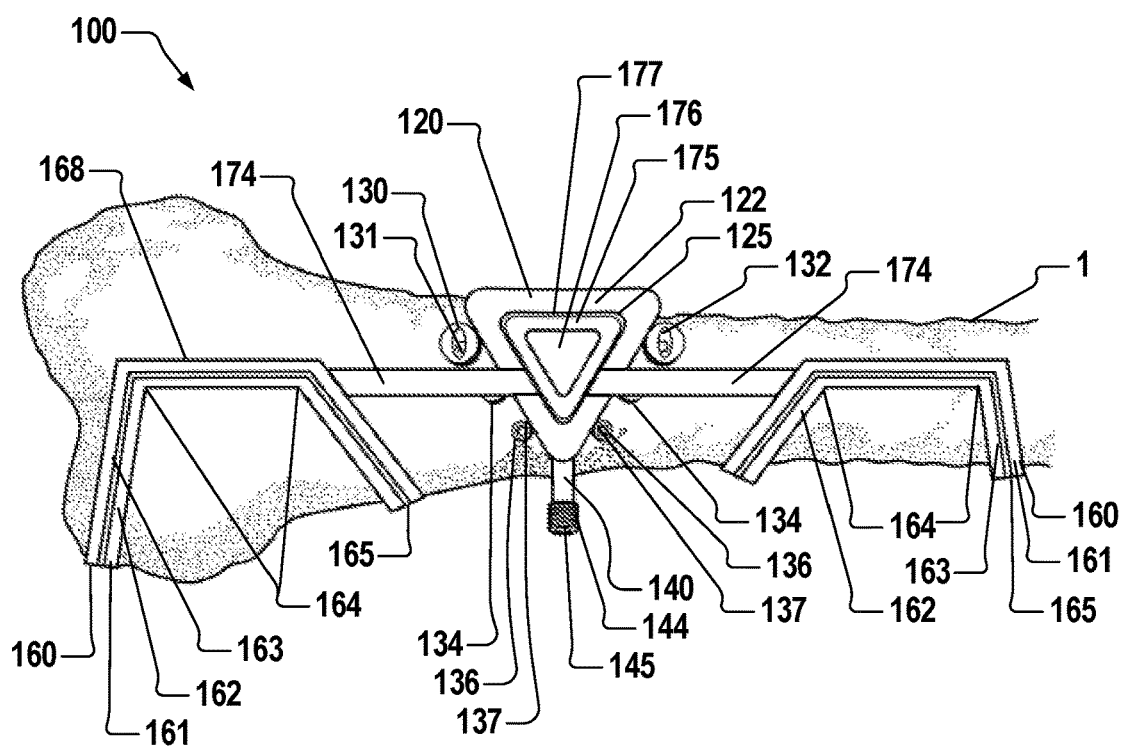
FIG. 11 is a top view of two cutting guides attached to one positioner.

FIG. 11 illustrates that one positioner 120 may be used to make additional cuts on the same bone 1 by attaching a second cutting guide 160, or more. The portion of bone 1 to which the positioner 120 is attached may even be separated from the remaining skeleton, and the accuracy of further cuts would remain, which would not be the case with currently available patient-specific instruments. This invention can also be used in craniomaxillofacial or veterinary applications. In addition to improved precision, this invention also circumvents the challenges incurred when there is soft tissue overlying the bone 1 to be cut. As the placement of the cutting guide 160 does not depend solely on matching the bone 1 surface anatomy, the potential for error due to overlying soft tissue is eliminated.

Figure 12:
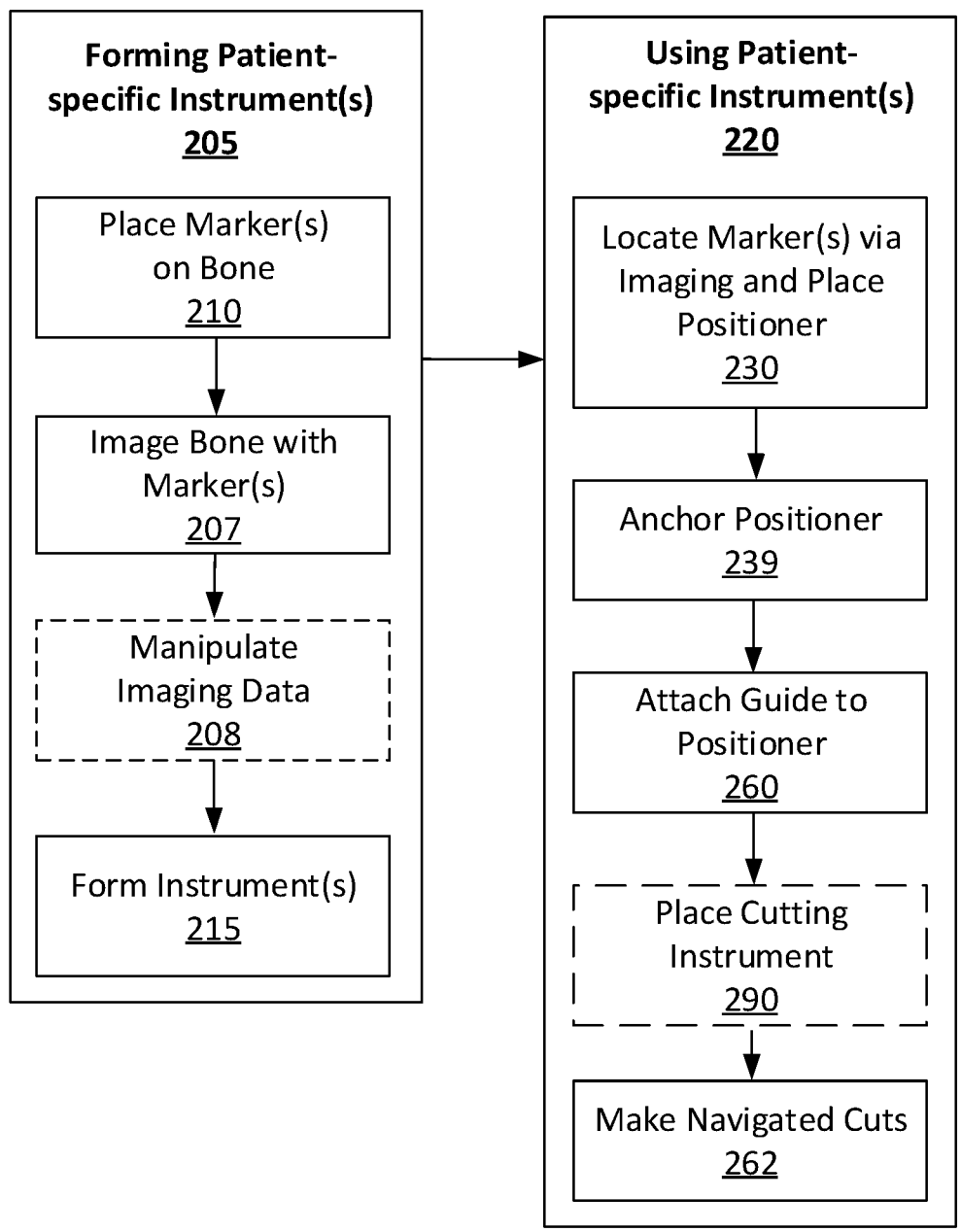
FIG. 12 is a flow chart showing a method(s) for making and using a cutting guide of the present invention.

FIG. 12 is a flow chart that shows the basic steps of the method(s) of forming and using a patient-specific cutting guide 200, including the positioner 120 and cutting guide 160 instruments. Methods of producing and/or using those instruments 205, 220 may include placing markers on bone 210, scanning or imaging the bone with markers 207, manipulating images and designing a patient-specific positioner and/or cutting guide 208 (including any manipulation and transfer of data), printing or otherwise forming one or both of those patient-specific tools 215, and correctly locating/orienting 230 and anchoring 239 the positioner 120 on the bone 1 as described above. Once the positioner's 120 position is confirmed using imaging 7, the cutting guide is attached 260 to the positioner 120. A cutting instrument is placed in the guide 290, and the bone 1 may be divided by making navigated cuts 262. Dashed boxes 208, 290 in FIG. 12 serve to indicate that the present invention is novel regardless of the specifics of data manipulation and types of cutting instruments and that a variety of configurations related to those specifics are contemplated herein. One of skill in the art will understand that these steps are not limited by their expression in FIG. 12, but include intermediate and/or alternative steps as described throughout the specification. The steps themselves may be subdivided, grouped, added to, or otherwise reordered provided that the resultant method provides comparable functionality.

Summary

In general, a system for a patient-specific bone cutting guide comprises at least two instruments. One is a positioner configured to locate at least one fiducial marker (placed on or near a patient's bone) and to be secured in three axes to prevent movement of the positioner on the bone. The second is a cutting guide configured to cooperate with the positioner and to delineate the cuts to be made in the bone. The positioner and the cutting guide are designed, formed, and configured from images taken of the patient's bone with one or more markers already in place. The marker(s) may or may not be considered part of the system, and the same is true of the imaging technology used to locate the marker(s). Such items may be provided separately or as a kit, along with any pegs or anchors.

The positioner may comprise at least three targeting apertures configured to locate at least three markers implanted in non-linear order. At least three anchoring apertures are configured to cooperate with any necessary anchors. The cutting guide comprises top surface contours that guide the depth of the cuts. Also, bottom surface contours that match the contours of the top surface of the bone may be utilized.

A method of forming a patient-specific bone cutting guide system comprises placing at least one marker on a patient's bone, imaging the patient's bone with the at least one marker in place, forming a positioner designed to incorporate the position of the at least one marker (where the positioner is configured to locate the at least one marker and to be anchored in place), and forming a cutting guide configured to be oriented by the positioner and to delineate the cuts to be made in the bone. This method may comprise placing at least three markers on the bone and forming the positioner with at least three targeting apertures, one of which is on a transverse member, and at least three anchoring apertures. Also, this method may simply comprise forming and configuring the positioner and the cutting guide from images taken of the patient's bone with at one or more markers already in place.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A cutting guide system comprising:
   (a) at least one marker configured to be placed on or near a patient's bone;
   (b) a positioner configured to locate the at least one marker and to be anchored to prevent movement thereof; and
   (c) a cutting guide configured to cooperate with the positioner and to delineate at least one cut to be made in the bone;
   wherein the positioner and the cutting guide are manufactured specifically for the patient based on images taken of the patient's bone with the at least one marker already in place;
   wherein said at least one marker is three markers; and
   wherein two of said three markers are configured to be placed along the longitudinal axis of the patient's bone and the third of said three markers is non-colinear.

2. The system of claim 1, wherein at least one of said at least one marker is configured to be placed on the patient's bone.

3. The system of claim 1, the positioner comprising at least three targeting apertures configured to locate said markers.

4. The system of claim 1, the positioner further comprising a transverse member configured to extend orthogonal to a longitudinal axis of the patient's bone.

5. The system of claim 1, the positioner further comprising at least three anchoring apertures.

6. The system of claim 1, further comprising anchors.

7. The system of claim 1, the cutting guide comprising top surface contours that guide the depth of the cuts.

8. The system of claim 1, the cutting guide comprising bottom surface contours configured to match the contours of the top surface of the bone.

9. The system of claim 1, further comprising an imaging technology configured to locate said markers during surgery.

10. The system of claim 1, further comprising a cutting instrument configured to cooperate with the cutting guide.

11. The system of claim 1, wherein said positioner and said cutting guide are configured as one piece.

12. The system of claim 1, wherein said positioner and cutting guide are manufactured via additive manufacturing techniques.

13. The system of claim 1, wherein said cutting guide includes a top surface having contours that guide the depth of intended cuts.

14. The system of claim 13, wherein said contours are configured to vary in dimension in proportion to surface contours of the patient's bone.

15. The system of claim 13, wherein said contours are configured as negatives of the back of the patient's bone.

16. The system of claim 1, wherein said cutting guide includes a bottom surface having contours that guide the depth of intended cuts.

17. The system of claim 16, wherein said bottom surface contours are configured to match the contours of the top surface of the bone on which said cutting guide rests.

18. The system of claim 1, wherein said cutting guide is non-adjustable.

19. A cutting guide system comprising:
(a) at least one marker configured to be placed on or near a patient's bone;
(b) a positioner configured to locate the at least one marker and to be anchored to prevent movement thereof; and
(c) a cutting guide configured to cooperate with the positioner and delineate at least one cut to be made in the bone;
wherein the positioner and the cutting guide are manufactured specifically for the patient based on images taken of the patient's bone with the at least one marker already in place;
wherein said cutting guide includes a top surface having contours that guide the depth of intended cuts; and
wherein said contours are configured as negatives of the back of the patient's bone.

20. The system of claim 19, wherein at last one of said at least one marker is configured to be placed on the patient's bone.

21. The system of claim 19, wherein said at least one marker is at least three markers.

22. The system of claim 21, further comprising at least three targeting apertures configured to locate said at least three markers.

23. The system of claim 19, the positioner further comprising a transverse member configured to extend orthogonal to a longitudinal axis of the patient's bone.

24. The system of claim 19, the positioner further comprising at least three anchoring apertures.

25. The system of claim 19, further comprising anchors.

26. The system of claim 19, the cutting guide comprising top surface contours that guide the depth of the cuts.

27. The system of claim 19, the cutting guide comprising bottom surface contours configured to match the contours of the top surface of the bone.

28. The system of claim 19, further comprising an imaging technology configured to locate one or more markers during surgery.

29. The system of claim 1, further comprising a cutting instrument configured to cooperate with the cutting guide.

30. The system of claim 19, wherein said positioner and said cutting guide are configured as one piece.

31. The system claim 19, wherein said positioner and cutting guide are manufactured via additive manufacturing techniques.

32. The system of claim 19, wherein said at least one marker is three markers.

33. The system of claim 31, wherein said three markers are non-colinear.

34. The system of claim 19, wherein said contours are configured to vary in dimension in proportion to surface contours of the patient's bone.

35. The system of claim 19, wherein said cutting guide includes a bottom surface having contours that guide the depth of intended cuts.

36. The system of claim 35, wherein said bottom surface contours match the contours are configured to of the top surface of the bone on which said cutting guide rests.

37. The system of claim 19, wherein said cutting guide is non-adjustable.

* * * * *